United States Patent
Chieh et al.

(10) Patent No.: US 10,842,550 B2
(45) Date of Patent: Nov. 24, 2020

(54) NON-INVASIVE THERMAL ABLATION DEVICE AND METHOD

(71) Applicant: Jen-Jie Chieh, Taipei (TW)

(72) Inventors: Jen-Jie Chieh, Taipei (TW); Shu-Hsien Liao, New Taipei (TW); Kai-Wen Huang, Taipei (TW); Wen-Cheng Kuo, Taipei (TW); Ming-Hsien Chiang, Taipei (TW)

(73) Assignee: Jen-Jie Chieh, Taipei (TW)

( * ) Notice: Subject to any disclaimer, the term of this patent is extended or adjusted under 35 U.S.C. 154(b) by 245 days.

(21) Appl. No.: 15/891,374

(22) Filed: Feb. 8, 2018

(65) Prior Publication Data

US 2019/0110829 A1 Apr. 18, 2019

(30) Foreign Application Priority Data

Oct. 13, 2017 (TW) .............................. 106135219 A

(51) Int. Cl.
| | |
|---|---|
| *A61B 18/00* | (2006.01) |
| *A61B 18/04* | (2006.01) |
| *H01F 27/28* | (2006.01) |
| *A61N 2/00* | (2006.01) |
| *H05B 6/10* | (2006.01) |
| *H05B 6/44* | (2006.01) |
| *A61N 2/02* | (2006.01) |
| *H01F 5/00* | (2006.01) |

(52) U.S. Cl.
CPC .............. *A61B 18/04* (2013.01); *A61N 2/004* (2013.01); *H01F 27/28* (2013.01); *H05B 6/105* (2013.01); *H05B 6/44* (2013.01); *A61B 2018/00577* (2013.01); *A61N 2/02* (2013.01); *H01F 5/00* (2013.01)

(58) Field of Classification Search
CPC ........... A61N 2/00; A61N 2/004; A61B 18/04
USPC ....................................................... 600/9–15
See application file for complete search history.

(56) References Cited

U.S. PATENT DOCUMENTS

| | | | | |
|---|---|---|---|---|
| 5,248,312 A | * | 9/1993 | Langberg | A61B 17/22 606/27 |
| 6,458,071 B1 | * | 10/2002 | Jacobson | A61N 2/02 600/9 |
| 8,430,805 B2 | * | 4/2013 | Burnett | A61N 2/006 600/13 |

(Continued)

FOREIGN PATENT DOCUMENTS

| | | |
|---|---|---|
| CN | 1381281 | 11/2002 |
| CN | 1678371 | 10/2005 |

(Continued)

OTHER PUBLICATIONS

"Office Action of China Counterpart Application", dated Feb. 3, 2020, pp. 1-9.

*Primary Examiner* — John P Lacyk
(74) *Attorney, Agent, or Firm* — JCIPRNET

(57) ABSTRACT

A non-invasive thermal ablation method is provided for heating a lesion area using a non-invasive thermal ablation device. The non-invasive thermal ablation method includes: generating a time-varying magnetic field in a lesion area including a liquid metal using a magnetic field-generating element of the non-invasive thermal ablation device to heat the lesion area. In addition, a non-invasive thermal ablation device for the method is also provided.

12 Claims, 3 Drawing Sheets

(56) References Cited

U.S. PATENT DOCUMENTS

| | | | | |
|---|---|---|---|---|
| 8,579,787 B2 * | 11/2013 | Shapiro | ............... | A61N 2/02 600/12 |
| 2010/0152763 A1 * | 6/2010 | Kim | ............ | A61H 39/08 606/189 |
| 2017/0265803 A1 | 9/2017 | Copty | | |

FOREIGN PATENT DOCUMENTS

| CN | 101416040 | 4/2009 |
|---|---|---|
| CN | 102421359 | 4/2012 |
| CN | 102814004 | 12/2012 |
| CN | 103315945 | 12/2014 |
| CN | 107137358 | 9/2017 |

* cited by examiner

NON-INVASIVE THERMAL ABLATION DEVICE AND METHOD

CROSS-REFERENCE TO RELATED APPLICATION

This application claims the priority benefits of Taiwan application serial no. 106135219, filed on Oct. 13, 2017. The entirety of the above-mentioned patent application is hereby incorporated by reference herein and made a part of this specification.

BACKGROUND OF THE INVENTION

Field of the Invention

The invention relates to a thermal ablation method, and more particularly, to a non-invasive thermal ablation device and method.

Description of Related Art

The treatment of tumors can generally be divided into curative and palliative treatments. The former includes, for instance, transplants, surgical resection, or ablation therapy, and the latter includes, for instance, transcatheter arterial chemoembolization (TAE or TACE), local radiotherapy, or the newly developed targeted therapy.

Currently, the most common means in curative treatment is radiofrequency ablation (RFA). RFA mainly includes inserting an electrode needle into the tumor via an RF generator and an RF electrode needle under the guidance of ultrasound. RF energy is released from the non-insulator portion of the electrode needle and is further converted into thermal energy via ion agitation, thus causing coagulation necrosis to local tissue.

However, if the heating temperature of the electrode needle is too high, tissue may be carbonized, and if the heating temperature is not high enough, the effective range of the treatment may be insufficient due to temperature gradient. Therefore, invasive RFA often cannot accurately and completely achieve treatment goal.

SUMMARY OF THE INVENTION

The invention provides a non-invasive thermal ablation device and method that can accurately perform a heat treatment on a tumor site.

The non-invasive thermal ablation device of the invention is used for heating a lesion area. The non-invasive thermal ablation device includes a magnetic field-generating element for generating a time-varying magnetic field in the lesion area, wherein a liquid metal is distributed in the lesion area.

In an embodiment of the invention, the magnetic field-generating element includes a Helmholtz coil and a power supply coupled to the Helmholtz coil. The Helmholtz coil includes a first coil and a second coil, and the power supply is used for providing a first alternating current to the first coil and providing a second alternating current to the second coil.

In an embodiment of the invention, the power supply is further used for adjusting at least one of the frequency of the first alternating current, the frequency of the second alternating current, and the amplitude of the time-varying magnetic field.

In an embodiment of the invention, the first coil and the second coil are respectively disposed at two opposite sides of the lesion area.

In an embodiment of the invention, the non-invasive thermal ablation device further includes a magnetic field sensor and a controller coupled to the magnetic field sensor. The magnetic field sensor is used for sensing a magnetic field distribution, wherein the magnetic field distribution is associated with the time-varying magnetic field. The controller is used for positioning the lesion area according to the magnetic field distribution.

In an embodiment of the invention, a ferromagnetic particle is evenly mixed in the liquid metal.

In an embodiment of the invention, the controller calculates the temperature of the ferromagnetic particle according to the time-varying magnetic field and the magnetic field distribution.

In an embodiment of the invention, the magnetic field-generating element is further used for generating a spatial gradient magnetic field in the lesion area to control the liquid metal in which a ferromagnetic particle is evenly mixed to move according to the spatial gradient magnetic field.

In an embodiment of the invention, the magnetic field-generating element includes a first coil array, a second coil array, and a power supply. The first coil array includes a plurality of first coils, and the second coil array includes a plurality of second coils. The power supply is coupled to the first coil array and the second coil array for providing a first alternating current to the first coils and providing a second alternating current to the second coils.

In an embodiment of the invention, the liquid metal includes a liquid gallium.

In an embodiment of the disclosure, the lesion area includes a biological tumor cell.

The non-invasive thermal ablation method of the invention is suitable for heating a lesion area via a non-invasive thermal ablation device, wherein the non-invasive thermal ablation device includes a magnetic field-generating element. The non-invasive thermal ablation method includes: generating a time-varying magnetic field in a lesion area via a magnetic field-generating element, wherein the lesion area includes a liquid metal.

In an embodiment of the invention, the magnetic field-generating element includes a Helmholtz coil, and the Helmholtz coil includes a first coil and a second coil. The step of generating the time-varying magnetic field in the lesion area via the magnetic field-generating element includes: providing a first alternating current to the first coil and providing a second alternating current to the second coil to generate the time-varying magnetic field.

In an embodiment of the invention, the non-invasive thermal ablation method further includes: adjusting at least one of the frequency of the first alternating current, the frequency of the second alternating current, and the amplitude of the time-varying magnetic field to control the temperature of the lesion area.

In an embodiment of the invention, the non-invasive thermal ablation method further includes: sensing a magnetic field distribution via a magnetic field sensor, wherein the magnetic field sensor is associated with the time-varying magnetic field; and positioning the lesion area according to the magnetic field distribution.

In an embodiment of the invention, a ferromagnetic particle is evenly mixed in the liquid metal.

In an embodiment of the invention, the non-invasive thermal ablation method further includes calculating the temperature of the ferromagnetic particle according to the time-varying magnetic field and the magnetic field distribution.

In an embodiment of the invention, the non-invasive thermal ablation method further includes generating a spatial gradient magnetic field in the lesion area via the magnetic field-generating element to control the liquid metal in which a ferromagnetic particle is evenly mixed to move according to the spatial gradient magnetic field.

In an embodiment of the invention, a liquid gallium is distributed in the lesion area before the magnetic field-generating element generates the time-varying magnetic field in the lesion area.

In an embodiment of the disclosure, the lesion area includes a biological tumor cell.

Based on the above, the non-invasive thermal ablation method and the non-invasive thermal ablation device provided in the embodiments of the invention heat a liquid gallium using a time-varying magnetic field to heat a lesion area in which the liquid gallium is distributed. As a result, a lesion area of the body can be heated without performing percutaneous surgery.

In order to make the aforementioned features and advantages of the disclosure more comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

In the embodiments of the invention, liver cancer tumor cells are exemplified to describe the non-invasive thermal ablation method of the invention. In general, biological tumor cells cause surrounding capillaries to significantly proliferate when being formed to absorb nutrients from the surrounding environment. In an embodiment of the invention, the area containing one or a plurality of biological tumor cells and surrounding capillaries proliferated in a significant amount is referred to as a lesion area. However, biological cells generally gradually die when heated to over 46 Celsius, and therefore the non-invasive thermal ablation method provided in an embodiment of the invention adopts the above property to readily heat tumor cells by controlling the time-varying magnetic field without heating via a percutaneous electrode needle.

Figure 1:
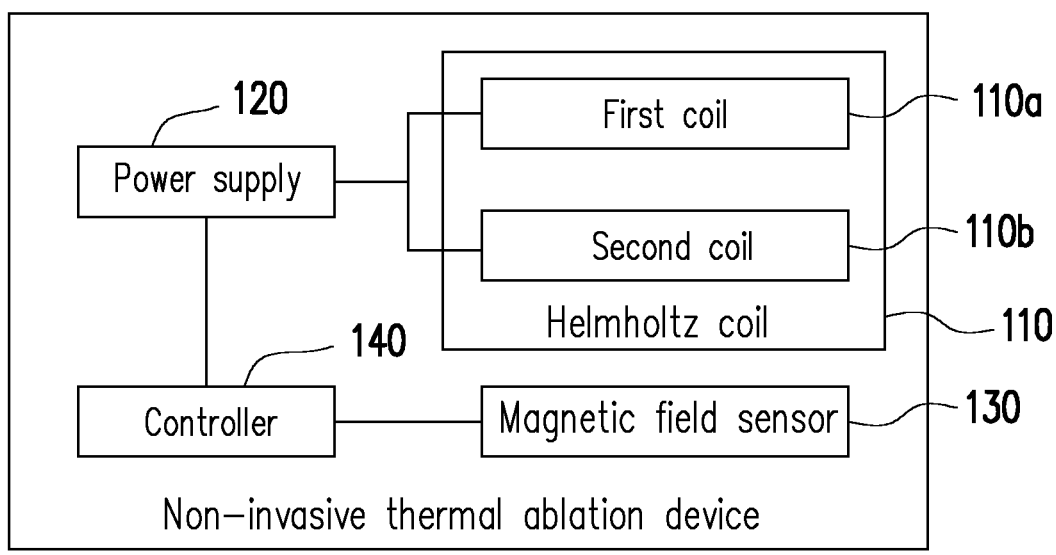
FIG. 1 illustrates a block diagram of a non-invasive thermal ablation device of an embodiment of the invention.

FIG. 1 illustrates a block diagram of a non-invasive thermal ablation device of an embodiment of the invention. Referring to FIG. 1, a non-invasive thermal ablation device 100 includes a magnetic field-generating element, a magnetic field sensor 130, and a controller 140, where the controller 140 is coupled to the magnetic field-generating element and the magnetic field sensor 130. The magnetic field-generating element is used for generating a time-varying magnetic field in a lesion area. In the present embodiment, the magnetic field-generating element is formed by a Helmholtz coil 110 and a power supply 120, where the power supply 120 is coupled to the Helmholtz coil 110. However, the invention is not limited thereto, and those having ordinary skill in the art can implement the magnetic field-generating element based on need or ability.

Figure 2B:
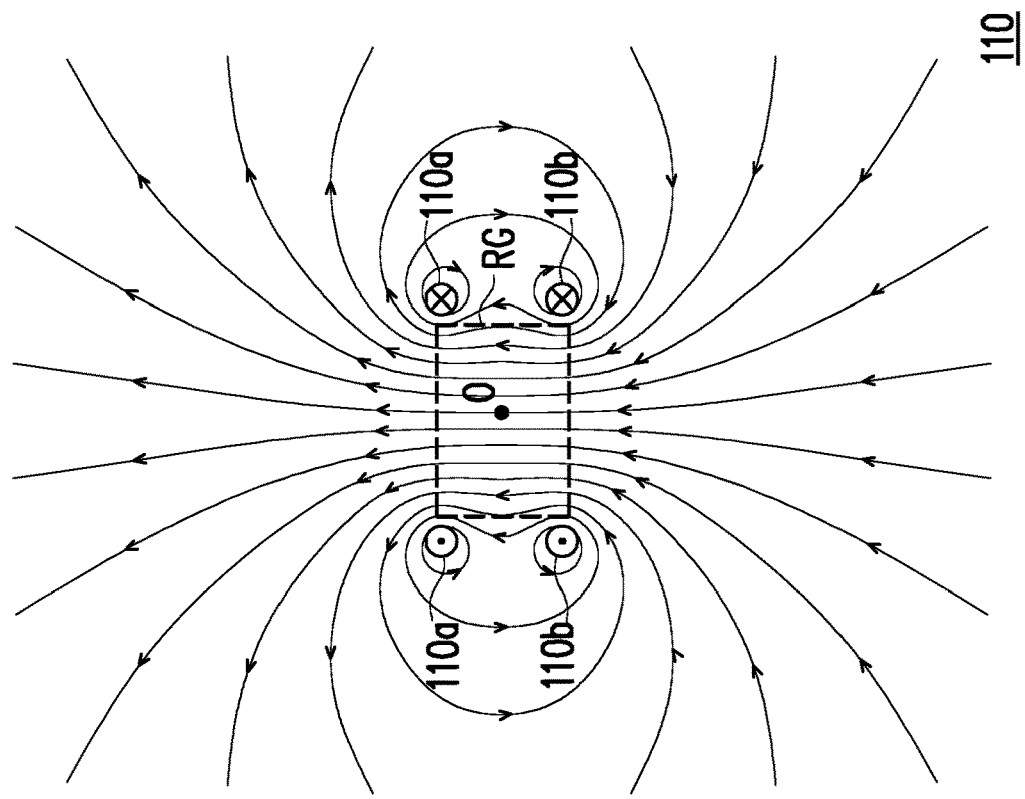
FIG. 2B illustrates a schematic of magnetic lines of flux generated by a Helmholtz coil of an embodiment of the invention.
Figure 2A:
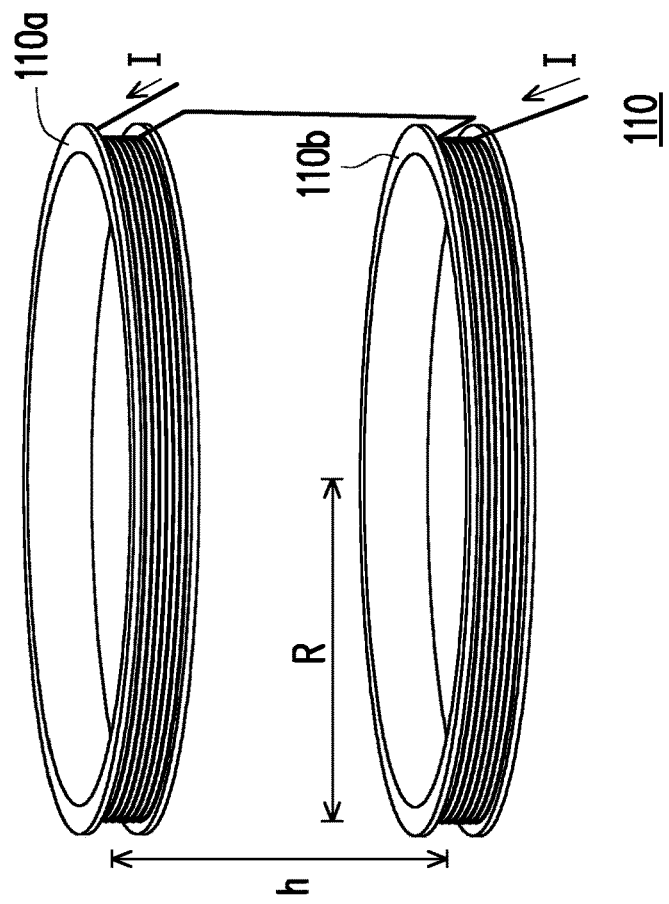
FIG. 2A illustrates a schematic of a Helmholtz coil of an embodiment of the invention.

FIG. 2A illustrates a schematic of a Helmholtz coil of an embodiment of the invention; FIG. 2B illustrates a schematic of magnetic line of flux generated by a Helmholtz coil of an embodiment of the invention.

The Helmholtz coil 110 includes a first coil 110a and a second coil 110b. As shown in FIG. 2A, the first coil 110a and the second coil 110b of the present embodiment are the exact same round conductor coils having a radius of R and a distance of h. When a current I in the same direction is applied to the first coil 110a and the second coil 110b, the magnetic field amplitude at a center point O of the two coils is calculated by Biot-Savart Law to be $$\left(\frac{4}{5}\right)^{\frac{3}{2}} \cdot \frac{\mu_0 nI}{R},$$

where $\mu_0$ is vacuum permeability, and n is the number of turns of each of the first coil 110a and the second coil 110b. As shown in the magnetic line of flux in FIG. 2B, a fairly uniform magnetic field is generated in an area RG between the two coils of the Helmholtz coil 110, and the magnetic field at each location in the area RG is almost equivalent to the magnetic field of the center point O.

The power supply 120 is coupled to the first coil 110a to provide a first alternating current to the first coil 110a, and coupled to the second coil 110b to provide a second alternating current to the second coil 110b. In the present embodiment, the frequencies and phases of the first alternating current and the second alternating current are the same, and therefore the magnetic field in the area RG between the two coils of the Helmholtz coil 110 is varied at the same frequency as the first alternating current and the second alternating current, and the magnetic field amplitude is positively correlated to the current intensity of the first alternating current and the second alternating current. Therefore, by adjusting the frequency and output current intensity of the power supply 120, the magnetic field frequency and magnetic field amplitude in the area RG can be correspondingly controlled. In the present embodiment, the power supply 120 can provide an alternating current having a frequency of at least 20 kHz.

Therefore, if the area RG includes a lesion area, then the magnetic field-generating element implemented by the Helmholtz coil 110 and the power supply 120 in the present embodiment can generate a time-varying magnetic field with controllable frequency and amplitude in the lesion area.

In an embodiment of the invention, with the controllable time-varying magnetic field generated by the magnetic field-generating element, the magnetic field sensor 130 and the controller 140 can be further used to accurately image and positioning the lesion area. The specific method is described in detail in the following embodiments.

Figure 3:
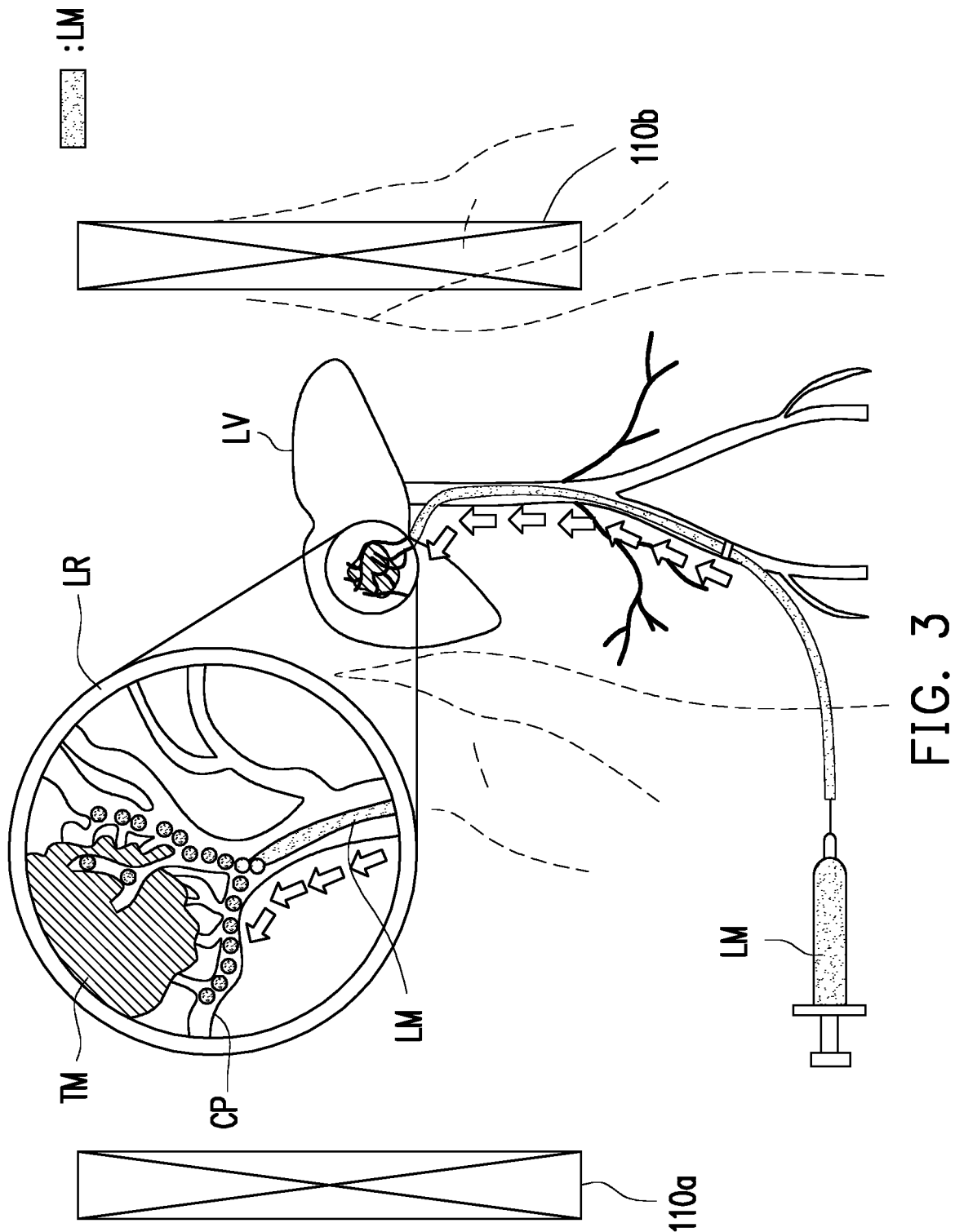
FIG. 3 illustrates a schematic of a non-invasive thermal ablation method of an embodiment of the invention.

FIG. 3 illustrates a schematic of a non-invasive thermal ablation method of an embodiment of the invention. The non-invasive thermal ablation method of the present embodiment is applicable to the non-invasive thermal ablation device 100 introduced in the embodiment of FIG. 1, and each element of the non-invasive thermal ablation device 100 is described below.

In the present embodiment, a liver LV includes a plurality of tumor cells TM, and many capillaries CP are proliferated around the tumor cells TM to form a lesion area LR. First, in the non-invasive thermal ablation method of the present embodiment, a liquid metal LM is distributed in the lesion area LR. In an embodiment, the liquid metal LM is, for instance, liquid gallium. Via the principle of embolization therapy, a significant amount of the liquid metal LM is accumulated in the capillaries CP after injection, such that the liquid metal LM is distributed in the lesion area LR. In an embodiment, a chemotherapy drug can be added in the liquid metal LM to further enhance efficacy. The chemotherapy drug is, for example, Adriamycin or Lipodox, but which is not limited herein. In other embodiments, the liquid metal LM can also be an alloy of liquid gallium metal or other liquid metals, and the invention is not limited thereto.

It should be mentioned that, since the density of the liquid metal LM is greater than the density of a regular embolic agent (such as lipiodol), the liquid metal LM is more readily accumulated in the capillaries CP. Moreover, after the treatment is complete, the liquid metal LM is more readily sucked out from the blood vessels.

Next, the non-invasive thermal ablation device 100 generates a time-varying magnetic field in the lesion area LR. In the present embodiment, the lesion area LR is placed between the first coil 110a and the second coil 110b. In other words, in the non-invasive thermal ablation method of the present embodiment, the first coil 110a and the second coil 110b are disposed at two opposite sides of the lesion area LR to generate a spatially-uniform and easy-to-control time-varying magnetic field in the lesion area LR. However, the invention is not limited thereto, and those having ordinary skill in the art can generate the time-varying magnetic field in the lesion area LR via other methods.

Since the liquid metal LM is distributed in the lesion area LR, the time-varying magnetic field generates an Eddy current in the liquid metal LM via electromagnetic induction, and the current is further converted into thermal energy. In general, a higher frequency of the time-varying magnetic field results in a greater induced electromotive force generated by electromagnetic induction, thus resulting in more thermal energy. Accordingly, in the present embodiment, by adjusting the frequency of the first alternating current provided to the first coil 110a and adjusting the frequency of the second alternating current provided to the second coil 110b, thermal energy generated by the liquid metal LM can be controlled. In an embodiment, the AC frequency provided by the power supply 120 is, for instance, 30 kHz, but the invention is not limited thereto. Those having ordinary skill in the art can adjust the AC frequency provided by the power supply 120 based on need (such as the distance between the two coils or the size of the tumor) or the magnetic field rate of change of the time-varying magnetic field.

It should be noted that biological cells gradually lose activity over 46 Celsius. As such, when the liquid metal LM is heated using the power supply 120 to kill tumor cells, the liquid metal LM can be controlled between 60 Celsius and 80 Celsius by controlling the AC frequency to achieve effective treatment and good treatment effect.

Moreover, the non-invasive thermal ablation device 100 of an embodiment of the invention further includes a magnetic field sensor 130 and a controller 140. As described above, the time-varying magnetic field generates an Eddy current in the liquid metal LM due to electromagnetic induction, and similarly, the Eddy current generates a magnetic field again due to current magnetic effect. Since the magnetic field generated by the first coil 110a and the second coil 110b can be estimated, when the magnetic field distribution between the first coil 110a and the second coil 110b is sensed using the magnetic field sensor 130, the controller 140 can image the liquid metal LM between the first coil 110a and the second coil 110b according to the resulting magnetic field distribution to position the lesion area LR.

It should be noted that, the thermal energy generated by the Eddy current in the liquid metal LM is not only positively correlated to the frequency of the time-varying magnetic field, but also positively correlated to the maximum magnetic field amplitude of the time-varying magnetic field. Therefore, if the positioning of the lesion area LR and the heating of the lesion area LR are to be separately preformed, then the lesion area LR can be positioned using a smaller maximum magnetic field amplitude, and the lesion area LR can be heated using a greater maximum magnetic field amplitude. For instance, a current 120 can provide a first alternating current and a second alternating current to the first coil 110a and the second coil 110b to generate a first time-varying magnetic field in the lesion area LR, where the maximum magnetic field amplitude thereof is 10 gausses for positioning the lesion area LR. Moreover, the current 120 can provide a first alternating current and a second alternating current to the first coil 110a and the second coil 110b to generate a second time-varying magnetic field in the lesion area LR, where the maximum magnetic field amplitude is 100 gausses for heating the lesion area LR.

As a result, the non-invasive thermal ablation device provided by an embodiment of the invention not only can heat the lesion area, but can also perform positioning before heating. In comparison to the traditional method of positioning metal using X-ray, the positioning method provided by an embodiment of the invention can reduce harm caused by radiation and reduce equipment cost.

In particular, in an embodiment of the invention, when liquid gallium is used as the liquid metal LM, the liquid gallium is further evenly mixed with a ferromagnetic particle (such as a nano-sized ferromagnetic particle). As a result, in addition to further increasing the efficiency of heating the lesion area LR via the Eddy current, the temperature of the lesion area LR can also be measured and the liquid metal LM can be moved using a magnetic field-generating element.

Specifically, particle collision caused by temperature causes the para-magnetism of the ferromagnetic particle to be reduced with increased temperature. When a time-varying magnetic field is applied, the magnetization of the ferromagnetic particle resonates with the frequency of the time-varying magnetic field. However, collision caused by temperature hinders the resonance of magnetization, which is reflected in the resonance frequency (such as third- and fifth-order) of the magnetization of the ferromagnetic particle. In short, the temperature of the ferromagnetic particle directly affects the magnetization thereof and the state of the time-varying magnetic field resonance.

Therefore, in an embodiment of the invention, after a controllable time-varying magnetic field is applied using the magnetic field-generating element, the magnetic field distribution function in the lesion area LR is obtained by the magnetic field sensor 130, and the controller 140 can calculate the temperature of the ferromagnetic particle by calculating the magnetization function of the ferromagnetic particle according to the magnetic field distribution function. Since the ferromagnetic particle is evenly mixed in the liquid metal, the calculation of the temperature of the ferromagnetic particle is equivalent to the calculation of the temperature of the liquid metal. As a result, when thermal ablation is performed on the lesion area LR, the temperature of heating the lesion area LR via the liquid metal can be further measured using the magnetic field sensor 130, and temperature distribution in the lesion area LR in which the liquid metal is distributed can be established.

Those having ordinary skill in the art should be able to obtain related teaching of how to estimate temperature via the resonance frequency during the magnetization of the magnetic particle from related literature of magnetism research.

In an embodiment, the magnetic field-generating element of the non-invasive thermal ablation device 100 includes, for instance, a first coil array formed by a plurality of first coils 110a and a second coil array formed by a plurality of second coils 110b. Since the first coil array and the second coil array can cover a greater range, the first coil array and the second coil array are, for instance, respectively located at two opposite sides of the lesion area LR or located at two opposite sides of the liquid gallium. In the present embodiment, the power supply 120 of the magnetic field-generating element is, for instance, respectively electrically connected to each of the first coils 110a in the first coil array and each of the second coils 110b in the second coil array to respectively provide a direct current with different current intensity to produce different magnetic field intensities at each location between the first coil array and the second coil array. In an embodiment, to move the liquid metal LM, the controller 140, for instance, controls the power supply 120 to establish a spatial gradient magnetic field between the first coil array and the second coil array.

For instance, when the user is to move the liquid metal (e.g., liquid gallium) of the first area in the lesion area LR to the second area in the lesion area LR, the power supply 120 can be controlled to provide different DC intensities such that a spatial gradient magnetic field is established between the first area and the second area of the first coil array and the second coil array to push the ferromagnetic particle in the liquid metal to the second area to drive the liquid metal to the second area. As a result, by controlling the power supply 120 in the non-invasive thermal ablation device 100 of an embodiment of the invention, the lesion area LR can be positioned and heated, and the liquid metal LM can also be moved to the desired area.

Based on the above, in the non-invasive thermal ablation device and the non-invasive thermal ablation method provided in an embodiment of the invention, liquid gallium metal is distributed in the capillaries proliferated around the tumor by utilizing the properties of the tumor itself, and liquid gallium metal is heated using a time-varying magnetic field. As a result, the tumor in the body can be heated without performing percutaneous surgery. Moreover, all tumor sites are heated due to the liquid gallium metal in the surrounding proliferated capillaries. Accordingly, numerous scattered tumors can also be heated at the same time to completely remove the tumors without affecting healthy cells in other areas. Moreover, via the non-invasive thermal ablation device provided in an embodiment of the invention, radiation such as X-ray is not needed to position tumor cells. As a result, not only is harm to the human body reduced, equipment cost is also reduced.

In an embodiment of the invention, a ferromagnetic particle is further evenly mixed in the liquid metal. Accordingly, in addition to conveniently moving the liquid metal to the desired area, the temperature of the liquid metal can also be readily measured, such that the frequency of the time-varying magnetic field can be adjusted to more accurately control the temperature during thermal ablation.

Although the invention has been described with reference to the above embodiments, it will be apparent to one of ordinary skill in the art that modifications to the described embodiments may be made without departing from the spirit of the invention. Accordingly, the scope of the invention is defined by the attached claims not by the above detailed descriptions.

What is claimed is:

1. A non-invasive thermal ablation device, adapted to heat a lesion area distributed with a liquid metal, the liquid metal being evenly mixed with a plurality of ferromagnetic particles and being accumulated in tissue cells of the lesion area, the non-invasive thermal ablation device comprising:
   a magnetic field-generating element, disposed at a distance away from the lesion area when heating the lesion area and configured to generate a first time-varying magnetic field in the lesion area for positioning the lesion area and a second time-varying magnetic field in the lesion area for heating the lesion area;
   a magnetic field sensor, configured to sense a magnetic field distribution due to an Eddy current generated by the liquid metal in the lesion area via electromagnetic induction, wherein the magnetic field distribution is associated with the first time-varying magnetic field; and
   a controller, coupled to the magnetic field sensor and configured to positioning the lesion area according to the magnetic field distribution, wherein the controller is further configured to control the magnetic field-generating element to generate the second time-varying magnetic field in the lesion area after positioning the lesion area, and a first magnetic field amplitude of the first time-varying magnetic field is smaller than a second magnetic field amplitude of the second time-varying magnetic field.

2. The non-invasive thermal ablation device of claim 1, wherein the magnetic field-generating element comprises:
   a Helmholtz coil, comprising a first coil and a second coil; and
   a power supply, coupled to the Helmholtz coil, and configured to provide a first alternating current to the first coil and provide a second alternating current to the second coil.

3. The non-invasive thermal ablation device of claim 2, wherein the power supply is further configured to adjust at least one of a frequency of the first alternating current, a frequency of the second alternating current, the first magnetic field amplitude of the first time-varying magnetic field, and the second magnitude field amplitude of the second time-varying magnetic field, wherein a maximum of the first magnetic field amplitude is 10 Gausses and a maximum of the second magnetic field amplitude is 100 Gausses.

4. The non-invasive thermal ablation device of claim 2, wherein the first coil and the second coil are respectively disposed at two opposite sides of the lesion area.

5. The non-invasive thermal ablation device of claim 1, wherein the controller calculates a temperature of the ferromagnetic particles distributed in the lesion area according to the first time-varying magnetic field and the magnetic field distribution, so as to obtain a temperature of heating the lesion area.

6. The non-invasive thermal ablation device of claim 1, wherein the magnetic field-generating element is further configured to generate a spatial gradient magnetic field in the lesion area to move the liquid metal in which the ferromagnetic particles are evenly mixed according to the spatial gradient magnetic field.

7. The non-invasive thermal ablation device of claim 6, wherein the magnetic field-generating element comprises:
- a first coil array, comprising a plurality of first coils;
- a second coil array, comprising a plurality of second coils; and
- a power supply, coupled to the first coil array and the second coil array, and configured to provide a first direct current to the first coils and provide a second direct current to the second coils.

8. A non-invasive thermal ablation method, adapted to heat a lesion area distributed with a liquid metal by a non-invasive thermal ablation device, wherein the liquid metal is evenly mixed with a plurality of ferromagnetic particles and is accumulated in tissues cells of the lesion area, the non-invasive thermal ablation device comprises a magnetic field-generating element, and the non-invasive thermal ablation method comprises:
- generating a first time-varying magnetic field in the lesion area by the magnetic field-generating element for positioning the lesion area;
- sensing a magnetic field distribution by a magnetic field sensor, wherein the magnetic field distribution is due to an Eddy current generated by the liquid metal in the lesion area via electromagnetic induction, and the magnetic field distribution is associated with the first time-varying magnetic field;
- positioning the lesion area according to the magnetic field distribution; and
- after positioning the lesion area, generating a second time-varying magnetic field in the lesion area by the magnetic field-generating element for heating the lesion area, wherein a first magnetic field amplitude of the first time-varying magnetic field is smaller than a second magnetic field amplitude of the second time-varying magnetic field,
- wherein the magnetic field-generating element is disposed at a distance away from the lesion area when heating the lesion area.

9. The non-invasive thermal ablation method of claim 8, wherein the magnetic field-generating element comprises a Helmholtz coil, and the Helmholtz coil comprises a first coil and a second coil, and the steps of generating the first and second time-varying magnetic fields in the lesion area by the magnetic field-generating element respectively comprise:
- providing a first alternating current to the first coil and providing a second alternating current to the second coil, in the first magnetic field amplitude, so as to generate the first time-varying magnetic field; and
- providing the first alternating current to the first coil and providing the second alternating current to the second coil, in the second magnetic field amplitude, so as to generate the second time-varying magnetic field after positioning the lesion area.

10. The non-invasive thermal ablation method of claim 9, further comprising:
- adjusting at least one of a frequency of the first alternating current, a frequency of the second alternating current, the first magnetic field amplitude of the first time-varying magnetic field, and the second magnitude field amplitude of the second time-varying magnetic field to control a temperature of the lesion area, wherein a maximum of the first magnetic field amplitude is 10 Gausses and a maximum of the second magnetic field amplitude is 100 Gausses.

11. The non-invasive thermal ablation method of claim 8, further comprising:
- calculating a temperature of the ferromagnetic particles distributed in the lesion area according to the first time-varying magnetic field and the magnetic field distribution, so as to obtain a temperature of heating the lesion area.

12. The non-invasive thermal ablation method of claim 8, further comprising:
- generating a spatial gradient magnetic field in the lesion area by the magnetic field-generating element, wherein the liquid metal in which the ferromagnetic particles are evenly mixed is moved according to the spatial gradient magnetic field.

* * * * *